United States Patent [19]

Sutton

[11] Patent Number: 5,053,443

[45] Date of Patent: Oct. 1, 1991

[54] METHODS OF PREPARING A POLYMERIC LATEX COMPOSITION AND WATER-INSOLUBLE BIOLOGICAL REAGENT

[75] Inventor: Richard C. Sutton, Rochester, N.Y.
[73] Assignee: Eastman Kodak Company, Rochester, N.Y.
[21] Appl. No.: 347,537
[22] Filed: May 4, 1989

Related U.S. Application Data

[63] Continuation-in-part of Ser. No. 136,214, Dec. 18, 1987, abandoned.

[51] Int. Cl.$^5$ ............................................... C08K 3/00
[52] U.S. Cl. ................................... 523/332; 430/628; 430/642; 424/78
[58] Field of Search .................... 523/332; 424/78; 430/628, 642

[56] References Cited

U.S. PATENT DOCUMENTS

| | | | |
|---|---|---|---|
| 3,853,987 | 12/1974 | Dreyer | 424/1 |
| 4,108,972 | 8/1978 | Dreyer | 424/1 |
| 4,127,499 | 11/1978 | Chen et al. | 252/301.17 |
| 4,199,363 | 4/1980 | Chen | 430/512 |
| 4,259,313 | 3/1981 | Frank et al. | 424/8 |
| 4,283,382 | 8/1981 | Frank et al. | 424/8 |
| 4,368,258 | 1/1983 | Fujiwhara et al. | 430/493 |

OTHER PUBLICATIONS

*Research Disclosure* Publication 15913; Jul. 1977, pp. 7–8.
*Research Disclosure* Publication 16468, Dec., 1977, pp. 75–80.

*Primary Examiner*—Joseph L. Schofer
*Assistant Examiner*—Peter Mulcahy

[57] ABSTRACT

A polymeric latex composition having a hydrophobe incorporated therein can be prepared using a novel latex "loading" method. This method includes providing a loadable latex, providing a hydrophobe dissolved in a water-miscible organic solvent, heating the loadable latex to about 30° to about 90° C. and gradually adding the hydrophobe solution to the heated loadable latex under conditions to keep the hydrophobe in solution and to "load" it into the latex particles. In preferred embodiments, the latex is surfactant-free and has particles which have outer reactive groups which are capable of reacting with free amine or sulfhydryl groups of a biological compound. Such latices can be used to prepare water-insoluble biological reagents having a biological compound attached to the particles.

13 Claims, No Drawings

METHODS OF PREPARING A POLYMERIC LATEX COMPOSITION AND WATER-INSOLUBLE BIOLOGICAL REAGENT

RELATED APPLICATION

This is a continuation-in-part of U.S. Ser. No. 136,214, filed Dec. 18, 1987, now abandoned.

FIELD OF THE INVENTION

This invention relates to a method for the preparation of novel compositions which contain both hydrophobic materials and polymeric latex particles. It also relates to a method for the preparation of water-insoluble biological reagents composed of biological compounds attached to the polymeric latex particles containing hydrophobic materials.

BACKGROUND OF THE INVENTION

Several techniques have been described and used to distribute hydrophobic compounds, particularly non-polymeric compounds, in polymeric latex particles. For example, U.S. Pat. No. 4,368,258 (issued Jan. 11, 1983, to Fujiwhara et al) describes various techniques for incorporating dye-forming compounds and ultraviolet light absorbers into latex particles for use in photographic materials. Generally, the techniques all involve mixing a hydrophobe in solid state, a water-miscible organic solvent and a polymeric latex. The latex purposely contains large amounts of dispersant (also known as a surfactant or emulsifier).

U.S. Pat. No. 4,199,363 (issued Apr. 22, 1980, to Chen) describes a process for "loading" hydrophobes into latex particles whereby the compounds are dissolved within a water-miscible organic solvent. The process generally comprises gradually adding a "loadable" latex (one designed to receive the hydrophobe) to an organic solvent solution of the hydrophobe in such a manner that the hydrophobe is distributed with the latex particles predominantly. The resulting loaded latex is used in various photographic materials. The loadable latex further contains a surfactant for minimizing coagulation of latex particles.

While U.S. Pat. No. 4,199,363 provides useful materials for use in various photographic materials, there is a need for incorporating hydrophobes in polymeric latex particles to which can be attached biological compounds for various biological processes and assays. For example, it would be useful to have insoluble dyed reagents for use in various assays, such as agglutination assays, for the determination of a ligand of some type. These reagents could include a latex containing dyed particles to which a receptor has been attached. A receptor is a biological or chemical compound which specifically reacts or binds to a ligand of interest. Examples of ligand and receptor include avidin and biotin, and antibodies against corresponding antigens.

In preparing such biological reagents, it has been found that the process described in U.S. Pat. No. 4,199,363 has serious drawbacks. The described process whereby loadable latex is gradually added to the hydrophobe solution is prone to coagulation if the addition process is not carefully controlled. However, the likelihood of coagulation can be minimized with the use of surfactants which protect the latex particles.

However, in the preparation of insoluble biological reagents containing a hydrophobe and a biological compound attached to the particles, the presence of surfactant in the latex adversely affects the activity of many biological compounds. For example, the presence of surfactant often interferes with the reaction of antibody with its corresponding antigen. Such interference inhibits accurate and sensitive detection of various ligands in important diagnostic and analytical procedures. Yet, the presence of a surfactant appears to be essential in the practice of the method of adding hydrophobe to latex particles which is described in U.S. Pat. No. 4,199,363.

It would be desirable to be able to incorporate hydrophobes into latex particles for use in the preparation of biological reagents without the use of surfactants.

SUMMARY OF THE INVENTION

The problems noted above have been overcome with a method for preparing a polymeric latex composition comprising:

A. providing a loadable latex comprising a continuous aqueous phase and a dispersed phase comprising loadable polymeric particles prepared from one or more ethylenically unsaturated polymerizable monomers, B. providing a solution of a hydrophobe dissolved in one or more water-miscible organic solvents, C. heating the loadable latex to a temperature of from about 30° to about 95° C., and D. gradually adding the hydrophobe solution to the heated loadable latex while retaining the hydrophobe in solution and the polymeric particles dispersed so that the polymeric particles and hydrophobe are brought into intimate association, and the water-miscible solvent is diluted with water to reduce the solubility of the hydrophobe in the continuous phase, whereby the equilibrium distribution of the hydrophobe is driven away from the continuous phase toward the polymeric particles of the dispersed phase.

Also provided by this invention is a method of preparing a water-insoluble biological reagent containing a detectable hydrophobe, the method comprising:

A. providing a loadable latex comprising a continuous aqueous phase and a dispersed phase comprising loadable polymeric particles prepared from one or more ethylenically unsaturated polymerizable monomers, at least one of the monomers having reactive groups which are capable of reacting with free amino or sulfhydryl groups of a biological compound, B. providing a solution of a detectable hydrophobe dissolved in one or more water-miscible organic solvents, C. heating the loadable latex to a temperature of from about 30° to about 95° C., D. gradually adding the hydrophobe solution to the heated loadable latex while retaining the hydrophobe in solution and the polymeric particles dispersed so that the polymeric particles and hydrophobe are brought into intimate association, and the water-miscible solvent is diluted with water to reduce the solubility of the hydrophobe in the continuous phase, whereby the equilibrium distribution of the hydrophobe is driven away from the continuous phase toward the polymeric particles of the dispersed phase to provide a latex of particles having the hydrophobe with the particles, and E. reacting the reactive groups of the particles with a biological compound having free amino or sulfhydryl groups to form a biological reagent, provided that either the loadable latex is provided essentially free of surfactant, or any surfactant present is removed prior to the reacting step E.

The present invention provides a reliable method for preparing loaded latices. By "loaded" is meant that a hydrophobe (that is, a hydrophobic compound) has been incorporated into preformed latex particles. This method avoids the likelihood of coagulation of particles prematurely and effectively incorporates relatively large amounts of hydrophobe, if desired, into the particles.

In a preferred embodiment, the method of this invention uses a loadable latex which is essentially surfactant-free. While it might be expected that the lack of a surfactant or other stabilizing material might be disadvantageous, it has been found that the latices used herein are stable and can be used to advantage in preparing insoluble biological reagents containing hydrophobes.

These advantages are achieved by heating the loadable latex to a temperature of from about 30° to about 95° C. followed by the gradual addition of the hydrophobe which is dissolved in a water-miscible organic solvent. This procedure is opposite that described in U.S. Pat. No. 4,199,363 where the hydrophcbe solution is added gradually to the surfactant-containing loadable latex. The novel method of this invention can be used to advantage because the loadable latex is heated to 30°–95° C. prior to adding the hydrophobe solution. Coagulation is thereby avoided, and the use of a surfactant can be avoided as well if so desired.

DETAILED DESCRIPTION OF THE INVENTION

The method of the present invention provides a means for preparing a latex containing one or more hydrophobic compounds incorporated therein. The resulting "loaded" latex is useful in a variety of products including, but not limited to, photographic, electrophotographic, diagnostic, therapeutic and clinical materials. Preferably, the latex is useful for preparing water-insoluble reagents having diagnostic or other biological and medical uses. Other uses would be apparent to a worker of ordinary skill in the art.

The loaded polymeric latex compositions prepared according to the practice of this invention are polymeric latices comprising a continuous aqueous phase and a dispersed phase (or discontinuous) phase comprising one or more hydrophobes (defined below) distributed in at least a portion of loadable polymeric particles prepared from one or more ethylenically unsaturated polymerizable monomers (defined below).

The method of loading the polymeric particles in a latex is generally as follows:

A loadable latex is provided with suitable agitation to minimize coagulation. Although it is not essential, if desired, the latex can be purified prior to use to remove any residual surfactants, initiators, reaction by-products (for example, initiator fragments) and unreacted monomers. In preferred embodiments, the latex is prepared in the absence of surfactants, in which case, purification may or may not be necessary.

A solution of one or more hydrophobes in one or more water-miscible organic solvents is also provided. If necessary, the solution can be continuously agitated to maintain solubility of the hydrophobe therein.

The loadable latex is heated to a suitable temperature which is generally above the glass transition temperature of the latex polymer so as to enhance molecular motion of the hydrophobe therein during the loading process. The temperature will depend upon the characteristics of the polymer as well as the natural affinity of the hydrophobe for it. Generally, the temperature is in the range of from about 30° to about 95° C.

Once the loadable latex has been suitably heated, the hydrophobe solution is gradually added thereto while retaining the hydrophobe in solution in the continuous phase and the particles and hydrophobe are brought into intimate association. The hydrophobe is then free to distribute itself between the continuous and dispersed phases based on its relative solubilities therein. Gradual addition of the hydrophobic solution is required so that the solvent is gradually diluted with water thereby reducing the solubility of the hydrophobe in the continuous phase, and shifting the equilibrium distribution of the hydrophobe away from the continuous phase toward the polymeric particles of the dispersed phase. In this manner, a suitable portion of the hydrophobe becomes dispersed or dissolved in the polymeric particles so that they are loaded with hydrophobe. Any precipitation of the hydrophobe or coagulation among polymeric particles is minimized or avoided entirely.

More specifically, the loadable latex is heated to a temperature of from about 30° to about 95° C., and preferably to a temperature of from about 40° to about 90° C. prior to addition of the hydrophobe solution. This heating is normally done under atmospheric pressure, although reduced pressures can be used if desired. It is important that the temperature be at or above the glass transition temperature (Tg) of the polymeric particles. In the case of core/shell particles described in more detail below, the temperature should be at or above the Tg of the core polymer to facilitate loading of the hydrophobe into the core. The loadable latex is usually stirred continuously during the heating and loading steps in order to minimize coagulation. However, vigorous agitation is to be avoided to minimize coagulation. Heating can be accomplished in any suitable manner including the use of high temperature baths or jackets external to the latex, or heating rods or coils within the latex.

The hydrophobe solution need not be heated in the practice of this invention. It is preferred to use it at ambient temperature. However, modest heating (that is, to less than the boiling point of the organic solvent) can be carried out if desired.

After heating the loadable latex, the hydrophobe solution (which can be heated or unheated) is gradually added to the latex as mentioned above. The rate is such that coagulation is minimized, but that sufficient organic solvent is available to lower the Tg of the polymer of the particles to facilitate hydrophobe dispersion within the particles. Thus, the rate of addition will depend somewhat on the polymer, solvent and hydrophobe being used. A worker skilled in the art could readily determine a suitable rate with routine experimentation. Generally, the rate of addition is in the range of from about 1 to about 50 ml/min, with a rate of from about 2 to about 30 ml/min being preferred.

The proportion of loadable latex to hydrophobe solution is generally maintained within the volume ratio of from about 30:1 to about 1:1, and preferably from about 15:1 to about 1.5:1. The weight ratio of hydrophobe in the hydrophobe solution to polymeric particles in the latex is generally from about 1:30 to about 1:1, and preferably from about 1:15 to about 1:4.

Optionally, additional water can be added to the loadable latex simultaneously or subsequent to addition of the hydrophobe solution. This water can be at the same or different temperature as the loadable latex. This additional dilution of the continuous phase with water may be useful to further reduce the likelihood of coagulation.

Other optional steps can be followed if desired, such as purification steps to remove unwanted materials (such as surfactant and residual monomers) from the loadable latex prior to use, or to remove residual solvent, surfactant and hydrophobe after the loading process. The equipment and procedures needed for such steps are well known to one skilled in the art. If the loaded latex is to be used to prepare a biological reagent (as described herein), any residual surfactant must be removed prior to attaching biological compounds to the latex particles.

The aqueous loadable latices which are useful as starting materials in the practice of this invention comprise an aqueous continuous phase and loadable polymeric particles as a dispersed phase. The latices are preferably essentially free of surfactant or other colloidal or polymeric dispersing agents which are generally used to keep latices from coagulation.

The loadable polymeric particles useful in this invention can be chosen from among those which meet the following test:

At 25° C., the loadable polymeric particles being tested must (a) be capable of forming a latex with water at a particle concentration of from about 0.2 to about 20 percent, based on total latex weight, and (b) when a 100 ml sample of the latex is then mixed with an equal volume of the water-miscible organic solvent to be employed in forming the loaded polymeric latex composition desired, stirred and allowed to stand for 10 minutes, it exhibits no observable coagulation of polymeric particles.

It will be appreciated that the loadable particles can comprise of a variety of different loadable polymers. The particles can be homogeneous, meaning they are composed of the same polymer throughout, or they can be composed of two or more polymers, such as core-/shell polymer particles, graft copolymers, and other embodiments readily apparent to one skilled in the art. Preferably, the particles are core/shell polymers which are described in more detail below.

The particles are composed of polymers which are prepared from one or more ethylenically unsaturated polymerizable monomers, of which hundreds are known, and others are readily prepared by a skilled worker in the art. Generally, the monomers include, but are not limited to, monomers of the following groups:

(i) Ethenic monomers of the formula:

wherein R is hydrogen, halo or vinyl, and $R^1$ is hydrogen, halo, substituted or unsubstituted lower alkyl (for example, methyl or ethyl), or cyano if R is hydrogen. Examples of such monomers include isoprene, chloroprene, 1,3-butadiene, propenenitrile, vinylidene chloride, vinyl chloride, vinyl fluoride, ethylene, propylene and acrylonitrile.

(ii) Vinyl monomers of the formula:

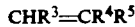

wherein $R^3$ and $R^4$ are independently hydrogen or substituted or unsubstituted lower alkyl (for example, methyl, chloromethyl or ethyl) and $R^5$ is a substituted or unsubstituted aryl group (generally of 6 to 14 carbon atoms in the aromatic ring, for example phenyl, tolyl, xylyl or naphthyl), a substituted or unsubstituted cycloalkyl (generally of 5 to 8 carbon atoms, for example, cyclopentyl, cyclohexyl, 4-methylcyclohexyl or cyclooctyl) or a substituted or unsubstituted heterocyclic group (generally of 5 to 7 carbon and heteroatoms in the ring, for example imidazolyl, pyrrolidonyl or pyridyl). Representative monomers of this formula include styrene, o-vinyltoluene, p-vinyltoluene, p-chlorostyrene, p-chloromethylstyrene, m-chloromethylstyrene, α-methylstyrene, 2,5-dimethylstyrene, 2-ethylstyrene, 2-vinylmesitylene, 1-vinylnaphthalene, 1-vinylimidazole, 4-vinylpyridine and t-butylstyrene.

(iii) Monomers which are 2-alkenoic acids or esters or anhydrides thereof which are generally of the formula:

wherein $R^6$ is hydrogen, $-COOR^8$ or substituted or unsubstituted lower alkyl (for example, methyl, carboxymethyl, chloromethyl, ethyl, propyl or t-butyl) and $R^7$ is hydrogen, halo or substituted or unsubstituted lower alkyl as described above. $R^8$ is hydrogen, substituted or unsubstituted alkyl or haloalkyl of 1 to 20 carbon atoms. Representative monomers of this formula include acrylic acid, methacrylic acid, butyl acrylate, methyl methacrylate, ethyl methacrylate, 2-ethylhexyl methacrylate and 2-acetoacetoxyethyl methacrylate.

(iv) Crosslinkable monomers, for example, those having two or more ethylenically unsaturated polymerizable groups, or those which are hardenable. Representative monomers are described in *Research Disclosure*, publication 19551, July, 1980, page 304 and include divinylbenzene, ethylene dimethacrylate, N,N'-methylenebisacrylamide, 2,2-dimethyl-1,3-propylene diacrylate, allyl acrylate, ethylidyne trimethacrylate and ethylene diacrylate.

(v) Ionic monomers having one or more anionic or cationic moieties, such as sulfates, sulfonates, phosphonates, carboxyl, quaternary ammonium groups and others known in the art. Representative monomers include sodium 2-acrylamido-2-methylpropanesulfonate, 2-carboxyethyl acrylate, styrenesulfonic acid, potassium salt and others known to one skilled in the art.

(vi) Monomers having requisite reactive groups which will directly or indirectly react with free amine or sulfhydryl groups of a biological compound such as an immunological compound, protein, enzyme or other compound of interest. Representative of such monomers include, but are not limited to, monomers having an active halogen atom (such as vinyl chloroacetate, chloroalkylated vinyl aromatics, for example chloromethylstyrene, or chloroalkyl acrylic or methacrylic esters, for example chloroethyl methacrylate, 3-chloro-2-hydroxypropyl methacrylate, and 3-chloropropyl acrylate), monomers having one or more pendant carboxyl groups or their functional equivalents (such as acrylic acid, methacrylic acid, itaconic acid, maleic acid or their anhydrides), monomers containing epoxy groups (such as glycidyl acrylate, glycidyl methacrylate, vinyl glycidyl ether or methallyl glycidyl ether), monomers containing isocyanate groups (such as isocyanatoethyl acrylate, isocyanatoethyl methacrylate, or α, α-dimethylmetaisopropenylbenzyl isocyanate), amine-containing monomers [such as 2-aminoethyl methacrylate, and N-(3-aminopropyl)methacrylamide], monomers containing an aziridine group [such as vinylcarbamoyl aziridine, acryloyl aziridine, methacryloyl aziridine, N-acryloylaziridine and 2-(1-aziridinyl)ethyl acrylate], monomers containing aldehyde groups (such as vinylbenzaldehyde or acrolein), 2-substituted ethylcarbonyl containing monomers (such as 2-chloroethyl acrylate, 2-chloroethyl methacrylate, 2-methylsulfonyloxyethyl methacrylate and 2-p-tolylsulfonyloxyethyl acrylate) or monomers having pendant activated 2-substituted ethylsulfonyl or vinylsulfonyl groups [such as those described in U.S. Pat. Nos. 4,161,407 (issued July 17, 1979 to Campbell) and 4,548,870 (issued Oct. 22, 1985 to Ogawa et al)] and others known to one skilled in the art.

Preferred monomers which can be used to prepare polymers useful in the practice of this invention include those having active halomethyl groups of 1 to 3 carbon atoms and the activated 2-substituted ethylsulfonyl and vinylsulfonyl monomers.

Preferred monomers having active halomethyl groups of 1 to 3 carbon atoms include chloromethylstyrene and bromomethylstyrene.

Preferred activated 2-substituted ethylsulfonyl and vinylsulfonyl monomers can be represented by the formula:

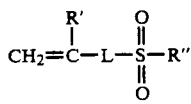

wherein R' is hydrogen or substituted or unsubstituted alkyl (generally of 1 to 6 carbon atoms, such as methyl, ethyl, isopropyl or hexyl. Preferably, R' is hydrogen or methyl.

R" is —CH=CHR'" or —CH$_2$CH$_2$X wherein X is a leaving group which is displaced by a nucleophile or is eliminated in the form of HX by treatment with a base (such as halo, acetoxy, alkylsulfonyloxy such as methylsulfonyloxy, arylsulfonyloxy such as p-tolylsulfonyloxy, trialkylammonio, for example, a trimethylammonio salt or pyridinio salt). R'" is hydrogen, substituted or unsubstituted alkyl (generally of 1 to 6 carbon atoms as defined for R'), or substituted or unsubstituted aryl (generally of 6 to 12 nuclear carbon atoms, such as phenyl, naphthyl, xylyl or tolyl). Preferably, R" is —CH$_2$CH$_2$X. This group, which is an activated 2-substituted ethyl group, can be substituted with any group which does not impair the displacement of the leaving group X.

L is a linking group which can be a substituted or unsubstituted alkylene generally having 1 to 20 carbon and hetero atoms in the backbone. This definition of alkylene is meant to include alkylene groups interrupted or terminated with oxy, thio, —NR$^9$— [wherein R$^9$ is hydrogen, substituted or unsubstituted alkyl of 1 to 6 carbon atoms (such as methyl, chloromethyl or 2-hydroxyethyl) or substituted or unsubstituted aryl of 6 to 10 carbon atoms (such as phenyl, naphthyl or xylyl)], ester (—COO—), amide (—CONH—),

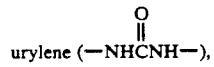

sulfonyl (—SO$_2$—), carbonate, sulfonamide, azo, phosphono or other similar groups. Representative alkylene groups include methylene, ethylene, isobutylene, hexamethylene, carbonyloxyethoxycarbonyl, methylenebis(iminocarbonyl), carbonyloxydodecylenecarbonyloxyethylene, carbonyliminomethyleneiminocarbonyliminoethylene, carbonyliminomethyleneiminocarbonylethylene and other groups described or suggested by U.S. Pat. Nos. 4,161,407 and 4,548,870, noted above.

L can also be substituted or unsubstituted arylene generally having 6 to 12 nuclear carbon atoms. Representative arylene groups include phenylene, tolylene, naphthylene and others noted in the patents mentioned above. Also included in this definition of L are divalent groups which are combinations of one or more of each of the alkylene and arylene groups defined above (for example, arylenealkylene, alkylenearylenealkylene and others readily determined by one of ordinary skill in the art). Preferably, L is substituted or unsubstituted phenylenealkylene, phenylenealkylene substituted with one or more alkyl groups (as defined for R'), alkoxy groups (generally of 1 to 6 carbon atoms, for example, methoxy, propoxy or butoxy) or halo groups, or carbonyliminomethyleneiminocarbonylethylene.

Representative useful monomers include m and p-(2-chloroethylsulfonylmethyl)styrene, m and p-[2-(p-tolylsulfonyloxy)ethylsulfonylmethyl]styrene, m and p-vinylsulfonylmethylstyrene, N-[m and p-(2-chloroethylsulfonylmethyl)phenyl]acrylamide, and N-[2-(2-chloroethylsulfonyl)ethylformamidomethyl]acrylamide. The first monomer is preferred.

The polymeric particles used in the practice of this invention are water-insoluble latex particles having a particle size greater than about 0.01 μmeters, preferably in the range of from about 0.01 to about 5 μmeters, and more preferably from about 0.1 to about 3 μmeters. The particles are present in the loadable latex in an amount of from about 0.2 to about 30 percent based on total latex weight. Preferably, the amount is from about 0.5 to about 15 weight percent.

Preferred particles are composed of at least two separate polymers, for example as a core/shell polymer or a graft copolymer. Core/shell polymers are particularly useful where the core polymer has a higher affinity for a loaded hydrophobe in comparison to the shell polymer. In addition, the shell polymer is particularly useful when it is prepared from monomers having the reactive groups described above.

In general, useful core polymers have a glass transition temperature (identified herein as $T_{g1}$) less than about 100° C., and preferably from about −25° to about 95° C., in order to facilitate solubilization and immobilization of the hydrophobe in the core polymer. This $T_{g1}$ is a calculated value determined using the following equation [with the glass transition temperature values in °K. (Kelvin) which can be readily converted to °C.]:

$$\frac{1}{T_{g1}} = \left[\frac{1}{(T_g)_{m1}}\right]X_1 + \left[\frac{1}{(T_g)_{m2}}\right]X_2 + \ldots + \left[\frac{1}{(T_g)_{mn}}\right]X_n$$

wherein m1, m2, . . . mn represent the individual monomers from which the first polymer is derived and identify the $T_g$ (°K.) of the homopolymer prepared from each individual monomer, $X_1, X_2, \ldots X_n$ represent the weight fractions of the monomers used to prepare the first polymer, and n represents the number of monomers used to prepare the first polymer.

Representative polymers of which the core of the particles can be composed include the following materials (the $T_{g1}$ values have been calculated for some of the polymers): poly(styrene-co-2-acetoacetoxyethyl methacrylate) (50:50, 70:30, 85:15 and 95:5 molar ratios, having $Tg_1$s of 27°, 47°, 69° and 91° C., respectively), poly(styrene-co-m and p-chloromethylstyrene-co-2-hydroxyethyl acrylate) (67:30:3 molar ratio), poly(styrene-co-n-butyl acrylate) (78.7:21.3 molar ratio, $Tg_1$ of 47° C.) and poly(styrene-co-benzyl acrylate) (90:10 molar ratio).

The shell of the particles comprises a second polymer which provides reactive sites for covalent bonding of the biological compound, and sufficient swellability in water-miscible organic solvents used in the loading of hydrophobe into the core of the particles without encouraging retention of the hydrophobe in the shell.

Generally, the second polymer has a $Tg_2$ which is equal to or greater than the term [$Tg_1$ less 10° C.]. $Tg_2$ is usually greater than $Tg_1$, but it can be equal to $Tg_1$, or as much as 10° C. less than $Tg_1$.

Representative polymers of which the shell of the particles can be composed include the following (the $Tg_2$ values have been determined for some of the materials): poly(m and p-chloromethylstyrene) ($Tg_2$ of 82° C.), poly(styrene-co-m and p-chloromethylstyrene-co-2-hydroxyethyl acrylate (67:30:3 molar ratio), poly(styrene-co-m and p-chloroethylsulfonylmethylstyrene) (95.5:4.5 molar ratio, $Tg_2$ of 105° C.), poly[styrene-co-N-[m and P-(2-chloroethylsulfonylmethyl)phenyl]acrylamide] (99.3:0.7 molar ratio), poly(m and p-chloromethylstyrene-co-methacrylic acid) (95:5, 98:2 and 99.8:0.2 molar ratio, $Tg_2$s of 85°, 83° and 82° C., respectively), poly(styrene-co-m and p-chloroethylsulfonylmethylstyrene-co-methacrylic acid) (93.5:4.5:2 molar ratio), poly[styrene-co-N-[m and p-(2-chloroethylsulfonylmethyl)phenyl]acrylamide-co-methacrylic acid] (97.3:0.7:2 molar ratio), poly(styrene-co-m and p-vinylbenzaldehyde) (95:5 molar ratio), poly(styrene-co-m and p-vinylbenzaldehyde-co-methacrylic acid) (93:5:2 molar ratio), poly(styrene-co-m and p-chloromethylstyrene) (70:30 molar ratio, $Tg_2$ of 96° C.) and poly(styrene-co-methacrylic acid) (90:10 molar ratio, $Tg_2$ of 113° C.).

The polymeric particles can be prepared using any suitable polymerization technique, including emulsion (including batch, semi-continuous and continuous) and suspension polymerization techniques, graft copolymerization, and others known to one skilled in the polymer chemistry art. Emulsion polymerization is preferred as it can be used to provide particles without the use of surfactants or emulsifiers as described for example in U.S. Pat. No. 4,415,700 (issued Nov. 15, 1983 to Batz et al) and *Research Disclosure* publication 15963 (July, 1977). *Research Disclosure* is a publication available from Kenneth Mason Publications, Ltd., The Old Harbourmaster's, 8 North Street, Emsworth, Hampshire P010 7DD, England. Continuous emulsion polymerization is the most preferred technique, as described in the noted *Research Disclosure* publication. Other details of preparatory methods can be found in U.S. Pat. Nos. 4,161,407 and 4,548,870, noted above.

More particularly, staged emulsion polymerization can be used to provide core/shell polymers composed of two different polymers. Emulsion polymerization of the core is carried to substantial completion by continuously adding reactants to a reaction vessel under standard conditions. Monomers and initiators needed to make the shell polymer are then continuously added to the vessel containing the latex of the core polymer. In this manner, the shell has a definite known composition rather than being a mixture of core and shell monomers. Representative details of preparing the core-shell polymeric particles useful in this invention are provided in the Example below.

The core polymer of the particle generally comprises from about 30 to about 80, and preferably from about 40 to about 70, weight percent of the particle.

Further details of the preferred core/shell polymer particles can be found in copending and commonly assigned U.S. Ser. No. 98,583, filed Sept. 18, 1987 by Sutton et al.

To be considered a hydrophobe as that term is used herein, the compound must be essentially insoluble in distilled water at 25° C. Preferably, the dissolved concentration of hydrophobe in water under those conditions should be less than about 0.5 percent by weight at 25° C., based on the weight of the water. Any such hydrophobe can be employed in the practice of this invention which is or can be dissolved in a liquid consisting of one or more water-miscible organic solvents. Preferably, the hydrophobe must be soluble in the liquid at a concentration of at least about 0.2 percent based on the total weight of the resulting solution.

Although the practice of the present invention is not limited to particular hydrophobes, various classes of compounds are particularly useful. These classes include various hydrophobic photographic addenda, insecticides, herbicides, miticides, rodenticides, vitamins, enzymes, hormones and other known in the art, for example, those described in U.S. Pat. No. 4,199,363 (noted above) and the references mentioned therein.

Particularly useful hydrophobes are those normally considered tracer materials in biological diagnostic and analytical procedures, such as radiolabeled compounds which emit gamma rays, bioluminescent compounds, chemiluminescent compounds, chromogens such as water-insoluble dyes and dye-formers (including leuco dyes, for example imidazoles), fluorescent compounds or dyes, for example rare earth chelates.

In a preferred embodiment of this invention, the tracer material is an aromatic dye or leuco dye which is solubilized in the core polymer of core/shell particles. Such dyes or dye-providing materials can be of any suitable color which is readily observed in an assay. Generally, they contain one or more aromatic or other moieties which render them soluble in organic solvents which are water-miscible. Such dyes are not considered water-soluble. Preferred aromatic dyes include azo dyes, such as Oil Red EGN (available from Aldrich Chemical Co.) and Kodak Oil Red O (available from Eastman Kodak Co.). Other useful dyes would be readily determined by a skilled chemist with routine experimentation by seeing which dyes have the desired organic solvent solubility and selective solubility in a particular core polymer. Particularly useful leuco dyes include the triarylimidazoles described, for example in U.S. Pat. No. 4,089,747 (issued May 16, 1978 to Bruschi) such as 2-(4-hydroxy-3,5-dimethoxyphenyl)-4,5-bis(4-methoxyphenyl)imidazole which provides a red dye upon reduction.

The amount of hydrophobe in the particles will depend upon the hydrophobe, polymer and intended use of the resulting loaded latex. Generally, for the core/-shell particles, the amount is generally in the range of from about 0.1 to about 15 percent, based on particle weight.

The water-miscible organic solvents useful in the practice of this invention are generally those which:

(a) can be dissolved in (that is, they are miscible in) distilled water at 20° C. to the extent of at least about 20 parts by volume of solvent in 80 parts by volume of water, (b) have boiling points (at atmospheric pressure) above about −10° C., (c) do not detrimentally react chemically with aqueous latices containing the loadable polymer particles which are useful in the practice of this invention, and (d) do not dissolve more than about 5 weight percent of such loadable polymer particles at 20° C.

Representative useful solvents include, but are not limited to, alcohols (for example, methanol, ethanol, isopropanol, ketones (for example, acetone, methyl ethyl ketone), amides (for example, dimethylformamide), nitriles (for example, acetonitrile), tetrahydrofuran, N-methyl-2-pyrrolidone, dimethyl sulfoxide and mixtures thereof. Of these, acetone, methanol and acetonitrile are preferred when the hydrophobe is soluble therein.

The amount of hydrophobe present in the hydrophobe solution can vary depending upon the hydrophobe, solvents and loadable latex used in the method. Generally, the hydrophobe is present in an amount of from about 0.05 to about 5 percent based on total solution weight.

The preparation of loaded latices is described in general terms above, and an example of a preferred procedure is provided in Example 1 below.

Once a loaded latex has been prepared, a biological compound of interest can be attached to the particles, assuming, of course, that the particles have surface reactive groups which are capable of reacting with the free amine or sulfhydryl groups of the compound.

The general procedure for preparing a biological reagent includes covalently attaching the biological compound of interest to the particles using generally known reactions. With many pendant groups, for example the haloalkyl, 2-substituted activated ethylsulfonyl and vinylsulfonyl, the compound can be directly attached to the particles. Generally, the polymer particles are mixed with the compound in an aqueous buffered solution (pH generally from about 6 to about 10) and a concentration of from about 0.01 to about 40 weight percent polymer particles (preferably from about 0.01 to about 10 weight percent). The amount of compound is at a ratio of compound to polymer of from about 0.1:1000 to about 1:10, and preferably from about 1:100 to about 1:10. Mixing is carried out at a temperature in the range of from about 5° to about 50° C., and preferably at from about 5° to about 40° C., for from about 0.5 to about 48 hours. Any suitable buffer can be used. The details of a representative preparatory procedure are illustrated in Example 2 below.

In some instances, the pendant reactive groups on the outer surface must be modified or activated in order to cause covalent attachment of the biological compound. For example, carboxyl groups must be activated using known carbodiimide chemistry, or using the carbamoylonium chemistry described in copending and commonly owned U.S. Ser. No. 98,429 entitled "Attachment of Compounds to Polymeric Particles Using Carbamoylonium Compounds", filed on Sept. 18, 1987 now abandoned by Sutton et al.

In other instances, an epoxy group on the outer surface can be hydrolyzed to form a diol compound capable of reacting with cyanogen bromide which can act as a coupling agent for amine groups in the biological compound. Aldehydes can react directly with amines to form a Shiff's base which can be subsequently reduced to form a covalent link. Alternatively, the aldehyde can be oxidized to an acid and chemistry identified above for carboxyl groups can be used to form an amide linkage.

The conditions of the reaction procedures described above are well known in the art and would require merely routine experimentation for implementing.

The following examples illustrate the practice of the present invention, but it is not to be construed as so limited.

EXAMPLE 1

Preparation of Loaded Latex

This example illustrates the preparation of a loadable latex of core/shell polymer particles, and the loading of a hydrophobe into it.

Preparation of Loadable Latex

The three solutions outlined below were continuously added to a 1300 ml vessel containing deoxygenated water at 80° C. at the indicated rates:

Solution 1: Styrene (103 g), 2-acetoacetoxyethyl methacrylate (91 g) and 1-dodecanethiol (1.9 g) at 1.08 g/min. for 180 minutes.

Solution 2: Ammonium persulfate (6.5 g) and distilled, deoxygenated water (651 g) at 2.13 g/min. for 300 minutes.

Solution 3: Sodium pyrosulfite (3.24 g) and distilled water (651 g) at 2.17 g/min. for 300 minutes.

After 180 minutes, Solution 1 was exhausted, and replaced with a solution of m and p-chloromethylstyrene (130 g) and 1-dodecanethiol (1.3 g) which was added at a rate of 1.08 g/min. for 120 minutes. The final reactor contents were 11.45% solids. After five days of dialysis, the latex was 8.7% solids, and the average size of the resulting core/shell particles was about 0.34 µm as measured by transmission electron microscopy.

Loading Hydrophobe into the Particles

Kodak Oil Red O Dye (available from Eastman Kodak Co.) (2.5 g) was dissolved in acetonitrile (150 g). To a 60 g sample of the dialyzed loadable latex described above was added distilled water (290 g), and the resulting mixture was heated to 70° C. with stirring. To the hot latex solution were added 30 g portions of the dye solution, one portion every 30 minutes, until all had been added. The resulting dispersion was filtered, stripped of residual acetonitrile under reduced pressure, and refiltered to yield 70 g of a 4.82% mixture of nonagglutinated core/shell particles having dye in the cores only. The dye content was determined spectrophotometrically to be 8.9% (based on polymer weight).

EXAMPLE 2

Preparation of a Biological Reagent

This example illustrates the practice of the present invention to prepare a biological reagent useful for the determination of Streptococcus A antigen.

Monoclonal antibodies to Streptococcus A antigen and casein were covalently immobilized on the particles of the loaded latex described in Example 1 as follows: to 0.6 ml of 50 mmolar borate buffer (pH 8.5) was added 0.1 mg of total protein comprised of a 10:1 mixture of anti-Strep A antibody (2.9 mg/ml solution in phosphate buffered saline solution, known in the art as PBS) and casein (10 mg/ml water). After mixing, 41.5 µl of a 5% suspension of the polymeric latex particles were added (to provide 0.3% solids) and the resulting solution was rotated (end-over-end) for 24 hours at 37° C. to effect covalent attachment of the antibody and the casein to the particles to form a biological reagent.

EXAMPLE 3

Preparation of hCG Biological Reagent

This example illustrates the preparation of a biological reagent useful for the determination of human chorionic gonadotropin (hCG).

Core/shell polymeric particles of a loadable latex were imbibed with Oil Red EGN dye according to the procedure shown in Example 1 above. The particle cores were composed of poly(styrene-co-2-acetoacetoxyethyl methacrylate) (85:15 molar ratio), and the particle shells were composed of poly(m and p-chloromethylstyrene-co-methacrylic acid) (99.8:0.2 molar ratio). The particles had an average diameter of about 0.32 micrometer.

Monoclonal antibodies to two different epitopic sites of hCG were covalently immobilized on these particles as follows: to 0.6 ml of 50 mmolar borate buffer (pH 8.5) were added 0.1 mg of 10:1 mixture of hCG antibody (2.9 mg/ml phosphate buffered saline solution) and casein (10 mg/ml water). After mixing, 41.5 µl of a 5% suspension of the latex particles described above were added and the resulting suspension was rotated (end-over-end) for 24 hours at 37° C. to effect covalent attachment of the antibodies and casein to the particles to form a biological reagent.

EXAMPLE 4

Loading Latex of Poly(styrene-co-m and p-chloromethylstyrene) Particles

This example illustrates the practice of this invention by loading the commercially available hydrophobe, KODAK Oil Red O dye, into a loadable latex comprising latex particles (0.42 µm average size) of poly(styrene-co-m and p-chloromethylstyrene) (77.3:22.7 molar ratio).

This method was carried out by adding water (26 g) to a sample of the latex (54 g, 1.87% solids). The latex was then heated to 70° C., followed by addition of a hydrophobe solution (20 g) comprising the dye (0.1 g) in acetonitrile at a rate of 5 g/min. After mixing the resulting dispersion for about one hour, it was filtered through a coarse filter and the acetonitrile was removed under reduced pressure. The loaded latex was then filtered through Reeves Angel 230 filter paper, yielding 54 g of loaded latex of dyed particles (1% solids).

EXAMPLE 5

Loading Latex of Poly(styrene-co-m and p-chloromethylstyrene-co-2-hydroxyethyl acrylate)

This example is similar to Example 4 except that the loadable latex comprised particles (0.77 µm average size) of poly(styrene-co-m and p-chloromethylstyrene-co-2-hydroxyethyl acrylate) (67:30:3 molar ratio).

To a sample of the latex (22 g, 2.2% solids), was added 68 ml of water. The latex was then heated to 80° C., and a hydrophobe solution (30 g) comprising KODAK Oil Red O dye (0.25 g) in acetonitrile was gradually added (6 g/min.) with mixing. The resulting dispersion was purified as described in Example 4, yielding 24 g of a loaded latex of dyed particles (0.64% solids, 9.2% dye by weight of particles).

EXAMPLE 6

Loading Leuco Dye into Latex Particles

This example illustrates the practice of the present invention to incorporate a hydrophobic leuco dye into the core of core/shell polymer particles.

A latex (12.25 g, 10.2% solids) containing core/shell polymer particles having a core of poly(styrene-co-2-acetoacetoxyethyl methacrylate) (70:30 mole ratio) and a shell of poly[styrene-co-m and p-(2-chloroethylsulfonylmethyl)styrene (60:40 molar ratio)-co-methacrylic acid] (94.5:4.5:1 molar ratio) was diluted with distilled water (71.09 ml). The particles had an average diameter of 1.50 µm. After heating to about 30° C. and while being moderately stirred (that is, without vigorous agitation), a leuco dye solution (0.56 g) was added to the latex.

This leuco dye solution consisted of 2-(4-hydroxy-2,3-dimethoxyphenyl)-4,5-bis-(4-methoxyphenyl)imidazole (1.66 g) and sodium meta bisulfite (0.1 g) dissolved in ethanol (100 ml) (2.24% solids). Additional sodium meta bisulfite (0.05 g) was then added to the resulting latex mixture. After moderate stirring for 15 minutes, the mixture was filtered through a milk filter. The resulting latex containing leuco dye "loaded" particles was obtained at 1.6% solids.

The invention has been described in detail with particular reference to preferred embodiments thereof, but it will be understood that variations and modifications can be effected within the spirit and scope of the invention.

I claim:

1. A process for preparing a polymeric latex composition comprising:
   A. providing a loadable latex comprising a continuous aqueous phase and a dispersed phase comprising loadable polymeric particles prepared from one or more ethylenically unsaturated polymerizable monomers, said loadable latex being essentially free of surfactant and colloidal or polymeric dispersing agents,
   B. providing a solution of a hydrophobe dissolved in one or more water-miscible organic solvents, said hydrophobe being soluble in distilled water in an amount of less than about 0.5 weight percent at 25° C. and being soluble in a water-miscible organic solvent in an amount of at least about 0.2 weight percent, and said hydrophobe being selected from the group consisting of radio-labeled compounds, bioluminescent compounds, chemiluminescent compounds, chromogens, fluorescent compounds or dyes, photographic addenda, insecticides, herbicides, miticides, rodenticides, enzymes, hormones and vitamins,
   C. heating said loadable latex to a temperature of from about 30° to about 95° C., and
   D. gradually adding said hydrophobe solution to said heated loadable latex while retaining said hydrophobe in solution and said polymeric particles dispersed so that said polymeric particles and hydrophobe are brought into intimate association, and said water-miscible solvent is diluted with water to reduce the solubility of said hydrophobe in said continuous phase, whereby the equilibrium distribution of said hydrophobe is driven away from said continuous phase toward said polymeric particles of said dispersed phase, said addition being accomplished with continuous stirring, but without vigorous agitation, of said loadable latex.

2. The method of claim 1 further comprising the steps of purifying and removing residual organic solvent after complete addition of said hydrophobe solution.

3. The method of claim 1 wherein said particles have reactive groups on their outer surfaces which are capable of reacting with free amine or sulfhydryl groups of a biological compound.

4. The method of claim 1 wherein said polymeric particles are present in said loadable latex in an amount of from about 0.2 to about 30 percent based on total latex weight.

5. The method of claim 1 wherein said polymeric particles have an average diameter of from about 0.01 to about 5 micrometers.

6. The method of claim 1 wherein said hydrophobe is selected from the group consisting of a chromogen, fluorescent compound, bioluminescent compound and chemiluminescent compound.

7. The method of claim 6 wherein said hydrophobe is a dye or leuco dye.

8. The method of claim 1 wherein said hydrophobe is present in said hydrophobe solution in an amount of from about 0.05 to about 5 percent based on total solution weight.

9. The method of claim 1 wherein said water-miscible organic solvent can be dissolved in distilled water at 20° C. to the extent of at least about 20 parts by volume in 80 parts by volume of water, has a boiling point above about −10° C., does not detrimentally react with said latex and does not dissolve more than about 5 weight percent of said polymeric particles at 20° C.

10. The method of claim 1 wherein said latex is heated to a temperature of from about 40° to about 90° C.

11. The method of claim 1 wherein said hydrophobe solution is added to said heated latex at a rate of from about 1 to about 50 ml/min.

12. The method of claim 1 wherein the volume ratio of said latex to said hydrophobe solution is from about 30:1 to about 1:1.

13. The method of claim 1 wherein the weight ratio of said hydrophobe to said polymer particles is from about 1:30 to about 1:1.

* * * * *